United States Patent [19]
Brittain

[11] Patent Number: 5,675,658
[45] Date of Patent: Oct. 7, 1997

[54] ACTIVE NOISE REDUCTION HEADSET

[76] Inventor: Thomas Paige Brittain, 2320 Lakeview Dr., Amarillo, Tex. 79109

[21] Appl. No.: 507,988

[22] Filed: Jul. 27, 1995

[51] Int. Cl.[6] .............................. A61F 11/06; H04R 25/00
[52] U.S. Cl. ........................... 381/72; 381/71; 381/183; 381/186; 381/187
[58] Field of Search ..................... 381/71, 72, 73.1, 381/74, 25, 183, 187, 186, 94, 67, 24, 205

[56] References Cited

U.S. PATENT DOCUMENTS

| | | | |
|---|---|---|---|
| 2,972,018 | 11/1961 | Hawley et al. ............... | 381/71 |
| 3,614,344 | 10/1971 | Gorike . | |
| 3,796,840 | 3/1974 | Ohta ........................ | 381/183 |
| 3,984,885 | 10/1976 | Yoshimura et al. ........... | 381/183 |
| 4,654,871 | 3/1987 | Chaplin et al. . | |
| 4,953,217 | 8/1990 | Twiney et al. . | |
| 5,001,763 | 3/1991 | Moseley . | |
| 5,117,461 | 5/1992 | Moseley . | |
| 5,134,659 | 7/1992 | Moseley . | |
| 5,138,663 | 8/1992 | Moseley . | |
| 5,148,887 | 9/1992 | Murphy .................... | 381/183 |
| 5,181,252 | 1/1993 | Sapiejewski et al. . | |
| 5,182,774 | 1/1993 | Bourk . | |
| 5,333,206 | 7/1994 | Koss ....................... | 381/183 |
| 5,426,719 | 6/1995 | Franks et al. ............... | 395/2.37 |
| 5,452,361 | 9/1995 | Jones ...................... | 381/94 |
| 5,497,426 | 3/1996 | Jay ........................ | 381/67 |
| 5,539,831 | 7/1996 | Harley ..................... | 381/171 |
| 5,600,729 | 2/1997 | Darlington et al. ........... | 381/71 |
| 5,604,813 | 2/1997 | Evans et al. ................ | 381/71 |

FOREIGN PATENT DOCUMENTS

| | | | |
|---|---|---|---|
| 0212840 | 3/1987 | European Pat. Off. . | |
| 5230418 | 8/1977 | Japan ...................... | 381/183 |
| 3195295 | 8/1991 | Japan ...................... | 381/94 |
| 3258099 | 11/1991 | Japan ...................... | 381/94 |
| 3274894 | 12/1991 | Japan ...................... | 381/94 |
| 4008099 | 1/1992 | Japan ...................... | 381/94 |
| 2172470 | 9/1986 | United Kingdom ............ | 381/94 |
| 2265790 | 10/1993 | United Kingdom ............ | 381/73.1 |
| 8900746 | 1/1989 | WIPO ...................... | 381/94 |

*Primary Examiner*—Curtis Kuntz
*Assistant Examiner*—Xu Mei
*Attorney, Agent, or Firm*—Stephen R. Greiner

[57] ABSTRACT

An active noise reduction headset including a headband and at least one earcup secured thereto. A microphone is mounted within the earcup for detecting and transducing acoustic pressure within the earcup to a corresponding microphone electronic signal. An electronic signal processing unit is mounted within the earcup and coupled with the microphone for generating an anti-noise signal from the microphone electronic signal. A first speaker is mounted within the earcup for receiving and acoustically reproducing an electronic anti-noise signal from the electronic signal processing unit. A second speaker is mounted within the earcup for receiving and acoustically reproducing an electronic communication signal.

9 Claims, 2 Drawing Sheets

ACTIVE NOISE REDUCTION HEADSET

FIELD OF THE INVENTION

The present invention relates generally to electrical audio signal processing devices and, in particular, to a headset for reducing the levels of acoustic noise entering the ear of a user in a high noise environment.

BACKGROUND OF THE INVENTION

Aviation communications have come a long way since the first historic flights at the turn of the century. The singular achievement of two-way voice communications via radio transceivers has virtually revolutionized aviation. The radio has made it possible to fly safely over great distances under all kinds of traffic and weather conditions. Thus, practically all modern aircraft have at least one two-way radio for providing communications capabilities.

Significant motor and wind noise frequently makes voice communication among those piloting aircraft difficult and, in some cases, hazardous if miscommunication occurs. Merely working in such an aircraft cockpit can become impossible if no shielding from the background noise is provided. Nevertheless, as a result of a continuing need to communicate within environments having high levels of ambient noise, various headsets utilizing an active noise reduction (ANR) approach have been developed wherein an anti-noise signal is generated and added to a desirable communications signal being applied to a headset. Upon being acoustically reproduced, the anti-noise signal tends to cancel the background or ambient noise within the region around the ear.

A typical ANR headset system includes a microphone placed within an earcup and closely adjacent a sound-generating transducer or speaker for noise reduction purposes. The microphone senses the acoustic noise field in the cavity formed by the earcup about the ear and produces an electronic signal output representative of that field. The signal output is phase inverted, filtered, and amplified in a feedback loop and then fed to the speaker which produces noise-cancelling acoustic signals of substantially the same amplitude and frequency but opposite in phase to the acoustic noise field waveforms. Consequently, when acoustically reproduced, the noise component of the microphone signal tends to acoustically cancel undesirable noise present in the cavity.

Due to the relative complexity and high cost of the prior art ANR headsets, many potential users have avoided their purchase and have continued to rely on passive noise attenuating systems. As is well known, a conventional passive noise attenuating headset does an acceptable job at attenuating higher frequency noise, but is not as effective at attenuating aircraft motor and wind noise that occur at frequencies below about 300 Hz. Literally thousands of aviators, then, have foregone the benefits of ANR technology. It is believed, however, that if existing, passive noise attenuating headsets could be readily modified to incorporate ANR circuitry, considerable cost savings over the prior art ANR headsets would be realized and ANR holdouts would be few.

SUMMARY OF THE INVENTION

In light of the problems associated with the prior art ANR headsets, it is a principal object of the present invention to provide a headset with active noise reduction capabilities that is inexpensive, dependable and fully effective in cancelling or nullifying ambient noise therein.

Briefly, the active noise reduction headset in accordance with this invention achieves the desired objects by featuring a headband and at least one earcup secured thereto. A microphone is mounted within the earcup for detecting and transducing acoustic pressure within the earcup to a corresponding microphone electronic signal. An electronic signal processing unit, mounted within the earcup and coupled with the microphone, generates an anti-noise signal from the microphone electronic signal. A first speaker is mounted within the earcup for receiving and acoustically reproducing an electronic anti-noise signal from the electronic signal processing unit. A second speaker is mounted within the earcup for receiving and acoustically reproducing an electronic communication signal.

The invention further features a unique baffle adapted to be readily secured to a vacant earcup of a conventional passive noise attenuating headset. The baffle carries ANR components which, when energized, cancel ambient noise within the earcup and simultaneously deliver an audio communications signal to a wearer. Thus, the baffle forms part of an active noise reduction assembly for providing passive noise attenuating headsets with ANR capabilities.

The foregoing and other objects, features and advantages of the present invention will become readily apparent upon further review of the following detailed description of the preferred embodiments, as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENTS

Figure 1:
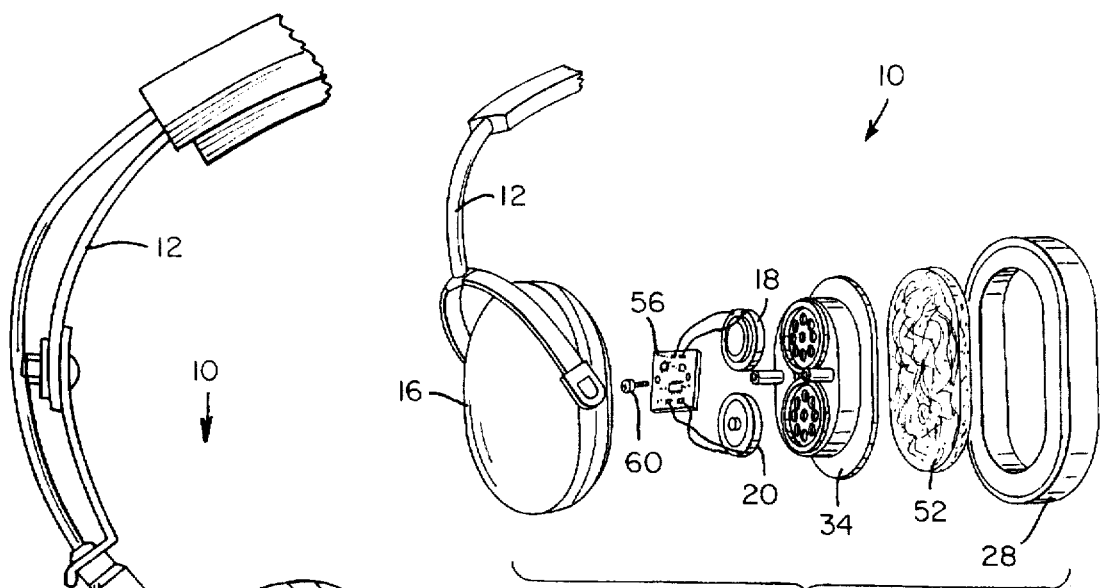
FIG. 1 is an exploded perspective view of an active noise reduction headset in accordance with the present invention.

As will be more completely described with reference to all of the accompanying drawings, the present invention is embodied in a novel headset generally designated 10 in FIG. 1. The preferred headset 10 is shown to include a headband 12 having an optional boom microphone 14, for receiving and transmitting speech of the headset wearer, and a pair of earcups 16 secured thereto in any known manner. (Since the earcups 16 are essentially mirror images of each other, only one earcup is shown in the FIGS. and will be discussed herein.) Mounted within each earcup 16 is an audio communication speaker 18 and a noise reduction speaker 20 which both receive and acoustically reproduce desired electronic signals. Disposed between the speakers 18 and 20 is an electret microphone 22 for generating an electronic signal representative of the acoustic reproductions from speakers 18 and 20 and ambient noise which may enter the cavity formed between the earcup 16 and the wearer.

The signal generated by the microphone 22 is provided to an electronic signal processing unit 24 which generates an anti-noise signal for acoustical reproduction by the noise reduction speaker 20 for cancelling or nullifying ambient noise in the earcup 16. As will be more particularly described in relation to FIG. 4, the anti-noise signal may be passed through a pair of cascaded filters for accentuating a desired frequency range prior to being provided to the noise reduction speaker 20. Through the electronic signal processing unit 24, an audio communications signal (if any) is also provided to the earcup 16 through communication speaker 18.

Figure 2:
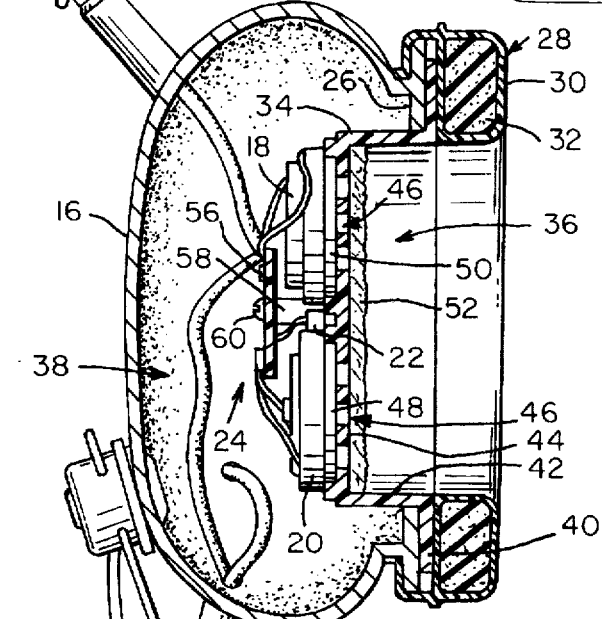
FIG. 2 is a lateral cross-sectional view of the active noise reduction headset.

Referring now to FIG. 2, the earcup 16 is shown to be provided with a peripheral flange 26 about its principal opening carrying a generally elliptical annular cushion 28 which contributes to the passive noise attenuating capabilities of the headset 10. Preferably, the cushion 28 comprises an elastomeric cover 30, filled with foam rubber 32, which may readily be secured over the flange 26. When pressed against the head of a wearer, the cushion 28 will envelop the wearer's ear thereby placing such in substantial acoustic isolation from the surrounding environment.

A baffle 34, preferably molded from thermoplastic material, separates the earcup 16 into an inside cavity 36 for positioning relatively close to the ear of a wearer and an outside cavity 38 opposite therefrom. Preferably, the baffle 34 includes a generally elliptical rim 40 for clamped engagement between the earcup flange 26 and attached cushion 28. Extending normally outward from the inner, peripheral edge of the rim 40 is a closed wall 42 of even height which supports, at its outermost edge, an integral speaker mounting plate 44.

Figure 3A:
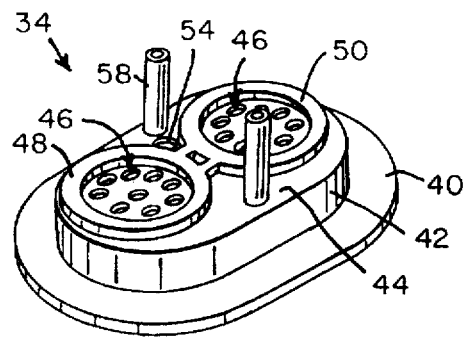
FIG. 3A is a preferred baffle for use in the headset.
Figure 3B:
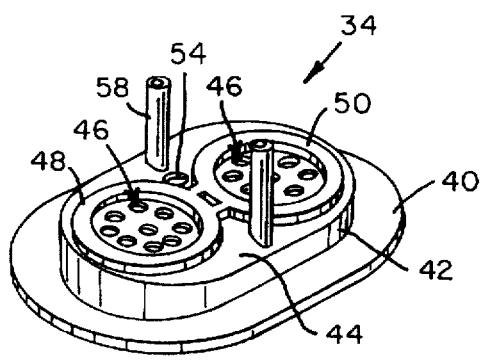
FIG. 3B is an alternative baffle for use in the headset having a sloping speaker mounting plate.

As shown in FIG. 3B, the closed wall 42 may be alternatively dimensioned along its perimeter to cast the rearward edge of the speaker mounting plate 44 in an outward direction relative to the forward edge thereof so as to conform to the natural incline of the external ear or auricle of a user and minimize, to the extent possible, the volume of the inside cavity 36. Thus, in the alternative embodiment, the mounting plate 44 slopes outwardly at a preferred angle of 12 degrees relative to the plane of the elliptical rim 40.

Preferably, the communication speaker 18 and the noise reduction speaker 20 are secured to the outer surface of the mounting plate 44 by a suitable adhesive cement. To optimize the acoustical coupling between the speakers 18 and 20 and the inside cavity 36, a cluster of openings or apertures 46 are provided in the mounting plate 44 adjacent each of the speakers. The material remaining between the closely-spaced apertures 46 of each cluster defines a grill of relatively high-strength for protecting the speakers 18 and 20 from inadvertent contact by a wearer.

As speaker manufacturers generally recommend a minimum clearance between a speaker and a protective barrier so that the speaker diaphragm is free to translate axially without obstruction, the outer surface of the mounting plate 44 is provided with a pair of integral risers 48 and 50 to support the speakers 18 and 20 at a fixed distance from their associated grills. As shown in the FIGS., then, each of the risers 48 and 50 surrounds a single cluster of apertures 46 and comprises a circular wall having a predetermined thickness and height, both preferably about 0.12 inches (3 mm), and a diameter substantially equivalent to that of the speakers 18 and 20. The speakers 18 and 20 are glued directly to the free end of each of the risers 50 and 48 respectively.

With reference back to FIG. 2, the noise reduction speaker 20 may be seen to be positioned directly beneath the communication speaker 18 in the lower half of the speaker mounting plate 44. In such a position, the noise reduction speaker 20 is oriented directly opposite the entrance to the ear canal of a wearer of the headset 10. Thus, the acoustic reproduction of an anti-noise signal by the noise reduction speaker 20 may be provided directly to the inner ear of a wearer with little distortion and maximum noise cancelling effect.

A soft pad 52 is positioned against the inner surface of the speaker mounting plate 44 to comfortably maintain the mounting plate at a predetermined distance from the ear pinna of a wearer. Preferably, the pad 52 is cut from a 0.125 inch (3.2 mm) thick sheet of felt material comprised of aramid fiber. In addition to being highly durable, aramid felt material has been found to attenuate high frequency acoustic energy within the inside cavity 36 and reduce undesirable feedback common in many prior art ANR systems.

With particular reference now to FIG. 3A, the preferred mounting plate 44 is shown to have a central aperture 54 positioned between the risers 48 and 50. The microphone 22 is secured by a suitable adhesive within the central aperture 54 so that its vented or open face is pointed through the central aperture toward the inside cavity 36 and ear canal of a wearer. So that the inside cavity 36 of the earcup 16 may be acoustically isolated from the outside cavity 38, the preferred adhesive is a silicon sealant material known for its significant bond strength and gap-filling properties. This sealant material may also be utilized to close substantially all of the usual vents (not shown) provided in the rear of each speaker 18 and 20 for acoustic isolation purposes.

The preferred distance between the microphone 22 and each speaker 18 and 20 is preferably less than 0.25 inches (6.4 mm) to avoid excessive phase lag in the headset system. When positioned in this fashion, the microphone 22 becomes acoustically coupled to each of the speakers 18 and 20 resulting in a minimal phase lag. Further, by mounting the microphone 22 to the plate 44 between the speakers 18 and 20 as described, the noise field within the ear canal of a wearer is detected to a maximum degree.

The anti-noise signal provided to the noise reduction speaker 20 is generated by the electronic signal processing unit 24 secured within each earcup 16. Preferably, the signal processing unit 24 is embodied in a portion of an electronic circuit, described more fully hereinbelow, mounted upon a rigid circuit board 56. A pair of integral posts 58, extending normally outward from opposite sides of the mounting plate 44, receive threaded fasteners 60 at their respective distal ends for securing the circuit board 56 to the baffle 34. As an economical substitute for the posts 58, a suitable, nonconductive mastic or putty material (not shown) may be utilized to bond the circuit board 56 to the outer portion of the mounting plate 44 as well as to the speakers 18 and 20.

Figure 4:
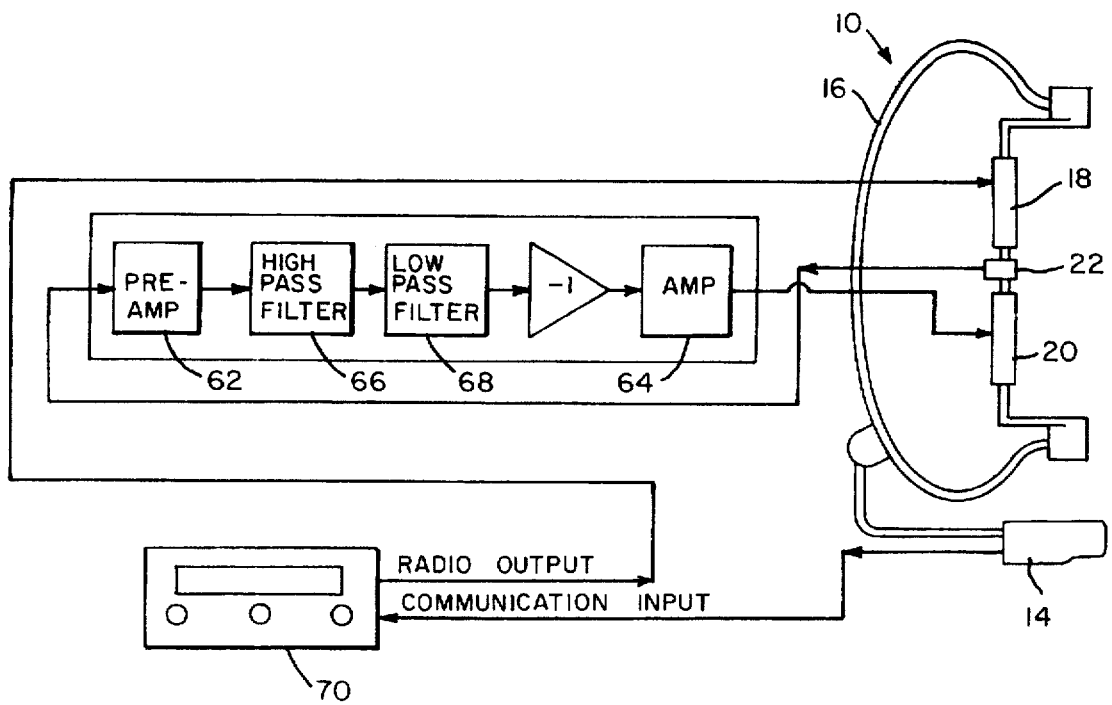
FIG. 4 is a schematic diagram showing the active noise reduction circuit of the headset.

During use of the headset 10, the microphone 22 generates an electronic signal representative of the total acoustic pressure received thereby which includes a combination of the acoustic output of the speakers 18 and 20 as well as the external ambient noise that has penetrated the inside cavity 36. As shown in FIG. 4, the electronic signal from the microphone 22 is amplified by a preamplifier 62, inverted, and then amplified by amplifier 64 to provide an anti-noise signal to the speaker 20 for cancelling the detected noise in the headset 10. This cancellation of noise is effective whether or not an additional radio communication signal (or similar signal) is also provided to the earcup 16 through the communication speaker 18.

The anti-noise signal is preferably further processed before it is presented to the noise reduction speaker 20. To this end, the anti-noise signal may be passed through a pair of cascaded filters 66 and 68 to accentuate a desired frequency range while minimizing undesirable phase characteristics. With continuing reference to FIG. 4, the pair of cascaded filters includes a high pass filter 66 for filtering out those components of the anti-noise signal having frequencies below a first frequency, and a low pass filter 68 for filtering out those components of the anti-noise signal having frequencies above a second frequency. In the preferred embodiment, the first frequency is in a range extending from 16 Hz to 70 Hz and the second frequency is in a range extending from 320 Hz to 3.4 kHz.

It should be understood that in the high pass filter 66 frequency components of the anti-noise signal falling below 16 Hz will be attenuated by a fixed amount and that the attenuation of the anti-noise signal will decrease linearly for frequency components falling between 16 Hz to 70 Hz at which no attenuation takes place. Similarly, in low pass filter 68 frequency components of the anti-noise signal falling above 3.4 kHz will be attenuated by a fixed amount and that the attenuation of the anti-noise signal increases linearly for frequency components falling between 320 Hz and 3.4 kHz at which maximum attenuation takes place. Since the high pass filter 66 and low pass filter 68 are in series, their net effect on the anti-noise signal is to pass signals in a range extending from 70 Hz to 320 Hz without loss. All higher and lower frequencies of the anti-noise signal are attenuated.

After passing through the high pass filter 66 and low pass filter 68, the filtered anti-noise signal is then provided to the amplifier 64 for amplification to a level appropriate for the noise reduction speaker 20. Of course, the amplifier 64 and equivalent components in the communication radio 70 may be adjusted with respect to one another to set the relative levels of the desired communication and anti-noise signals.

From the foregoing, it should be readily apparent that the active noise reduction headset 10 may be manufactured for purchase by a consumer as a ready-to-use product. Nevertheless, it is contemplated that the headset 10 may be sold in the form of a kit for providing a conventional passive noise reduction headset with ANR capabilities. Thus, in kit form, the invention would include all of the elements of the invention hereinabove described except the headband 12, optional boom microphone 14, and earcups 16 which are all of well known construction. The baffles 34, carrying the speakers 18 and 20 as well as the electronic signal processing units 24, would be installed in the passive noise reduction headset, after removing its original communication speakers, substantially in the manner shown above. The only required modification to the existing passive noise reduction headset is the drilling of a hole in one of the earcups to permit the passage of an electrical lead to provide a suitable source of power to each of the interconnected electronic signal processing units 24 typically required for a given headset installation.

While the invention has been described with a high degree of particularity, it will be appreciated by those skilled in the art that numerous modifications and substitutions may be made thereto. Therefore, the present invention is not limited to the various embodiments described herein, but encompasses any and all embodiments within the scope of the following claims.

I claim:

1. An active noise reduction headset, comprising:
    a headband;
    an earcup secured to said headband, said earcup having a peripheral flange and a cushion secured to said flange;
    a baffle secured to said earcup, said baffle separating said earcup into an inside cavity for positioning relatively close to the ear of a wearer and an outside cavity opposite therefrom, said baffle including:
        an elliptical rim adapted to engage said peripheral flange of said earcup, said elliptical rim having a central opening therein;
        a closed wall extending from said elliptical rim about said central opening, said closed wall adapted to project into said earcup; and,
        a speaker mounting plate secured to said closed wall, said speaker mounting plate having a plurality of apertures therethrough;
    a microphone mounted upon said baffle and positioned substantially within said outside cavity of said earcup for detecting and transducing acoustic pressure within said earcup to a corresponding microphone electronic signal;
    an electronic signal processing unit mounted upon said baffle and positioned substantially within said outside cavity of said earcup and coupled with said microphone for generating an anti-noise signal from said microphone electronic signal;
    a first speaker mounted upon said baffle proximate the center of one of said apertures in said speaker mounting plate and positioned substantially within said outside cavity of said earcup for receiving and acoustically reproducing an electronic anti-noise signal from said electronic signal processing unit; and,
    a second speaker mounted upon said baffle proximate the center of another one of said apertures in said speaker mounting plate and positioned substantially within said outside cavity of said earcup for receiving and acoustically reproducing an electronic communication signal.

2. The active noise reduction headset according to claim 1 wherein said microphone is positioned between said first speaker and said second speaker.

3. The active noise reduction headset according to claim 1 wherein said elliptical rim and said closed wall are positioned in separate planes which converge at an acute angle.

4. The active noise reduction headset according to claim 3 wherein said baffle further includes at least one post extending from speaker mounting plate to a free end remote therefrom for carrying said electronic signal processing unit.

5. The active noise reduction headset according to claim 3 wherein said speaker mounting plate further includes a pair of integral risers surrounding said apertures for supporting said first speaker and said second speaker at a fixed lateral distance from said apertures.

6. An active noise reduction assembly for positioning upon an earcup, the earcup having a principal opening and a peripheral flange around the principal opening, said active noise reduction assembly comprising:
    a baffle adapted to engage the earcup and bridge the principal opening thereof, said baffle including:
        an elliptical rim adapted to engage the peripheral flange of the earcup, said elliptical rim having a central opening therein;
        a closed wall extending from said elliptical rim about said central opening, said closed wall adapted to project into the earcup; and,
        a speaker mounting plate secured to said closed wall, said speaker mounting plate having a plurality of apertures therethrough;
    a microphone mounted upon said speaker mounting plate for detecting and transducing acoustic pressure within the earcup to a corresponding microphone electronic signal;

an electronic signal processing unit mounted upon said speaker mounting plate and coupled with said microphone for generating an anti-noise signal from said microphone electronic signal;

a first speaker mounted upon said speaker mounting plate proximate the center of one of said apertures in said speaker mounting plate for receiving and acoustically reproducing an electronic anti-noise signal from said electronic signal processing unit; and, a second speaker mounted upon said speaker mounting plate proximate the center of another one of said apertures in said speaker mounting plate for receiving and acoustically reproducing an electronic communication signal.

7. The active noise reduction headset according to claim 6 wherein said microphone is mounted on said speaker mounting plate between said first speaker and said second speaker.

8. The active noise reduction headset according to claim 6 wherein said elliptical rim and said closed wall are positioned in separate planes which converge at an acute angle.

9. The active noise reduction headset according to claim 6 wherein said baffle further includes at least one post extending from speaker mounting plate to a free end remote therefrom for carrying said electronic signal processing unit.

* * * * *